US012184799B2

(12) United States Patent
Larmuseau

(10) Patent No.: US 12,184,799 B2
(45) Date of Patent: Dec. 31, 2024

(54) SUMMARIZING A GENOMIC DATA ENTRY

(71) Applicant: KONINKLIJKE PHILIPS N.V., Eindhoven (NL)

(72) Inventor: Adriaan Joris H. Larmuseau, Shanghai (CN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 293 days.

(21) Appl. No.: 17/628,586

(22) PCT Filed: Jul. 21, 2020

(86) PCT No.: PCT/EP2020/070497
§ 371 (c)(1),
(2) Date: Jan. 20, 2022

(87) PCT Pub. No.: WO2021/013813
PCT Pub. Date: Jan. 28, 2021

(65) Prior Publication Data
US 2022/0255761 A1    Aug. 11, 2022

(30) Foreign Application Priority Data

Jul. 24, 2019  (WO) ............... PCT/CN2019/097490
Aug. 29, 2019  (EP) ................................... 19194491

(51) Int. Cl.
*H04L 9/00* (2022.01)
*G16B 50/40* (2019.01)
*H04L 9/32* (2006.01)

(52) U.S. Cl.
CPC ............. *H04L 9/50* (2022.05); *G16B 50/40* (2019.02); *H04L 9/3218* (2013.01)

(58) Field of Classification Search
CPC .......... H04L 9/50; H04L 9/3218; G16B 50/40
See application file for complete search history.

(56) References Cited

U.S. PATENT DOCUMENTS

| 2012/0005098 A1 | 1/2012 | Gross et al. |
| 2012/0005198 A1 | 1/2012 | Pontier et al. |

(Continued)

OTHER PUBLICATIONS

Belenkiy et al. "P-signatures and Noninteractive Anonymous Credentials." Theory of Cryptography: Fifth Theory of Cryptography Conference. Mar. 19-21, 2008. p. 356-374 (Year: 2008).*

(Continued)

*Primary Examiner* — Catherine Thiaw
*Assistant Examiner* — Zhe Liu

(57) ABSTRACT

Some embodiments are directed to a device (101) for determining a summary of a genomic data entry describing one or more genomic sequences. The summary is for offering the genomic data entry to one or more other parties. The device obtains the genomic data entry and analyse the genomic data entry to verify whether it satisfies one or more predefined properties. The device computes a cryptographic commitment to the genomic data entry. For each satisfied property of the one or more predefined properties, the device constructs a non-interactive zero-knowledge proof (NIZK) proving that the cryptographic commitment commits to a genomic data entry satisfying the satisfied property. The device associates the NIZKs with the cryptographic commitment to obtain a summary of the genomic data entry.

13 Claims, 5 Drawing Sheets

(56) References Cited

U.S. PATENT DOCUMENTS

| | | | |
|---|---|---|---|
| 2012/0297198 A1* | 11/2012 | Danezis | H04L 9/3247 |
| | | | 713/179 |
| 2015/0154646 A1 | 6/2015 | Mishra et al. | |
| 2017/0005787 A1* | 1/2017 | Weaver | G16B 50/40 |
| 2018/0083780 A1 | 3/2018 | Alesiani et al. | |
| 2019/0068374 A1* | 2/2019 | Veeningen | G06F 16/90344 |
| 2020/0202038 A1* | 6/2020 | Zhang | G16B 30/10 |
| 2020/0227160 A1* | 7/2020 | Youngblood | G16H 50/20 |
| 2020/0228339 A1* | 7/2020 | Barham | H04L 9/0869 |
| 2021/0075610 A1* | 3/2021 | Covaci | H04L 9/085 |
| 2021/0271982 A1* | 9/2021 | Lee | G06F 16/2365 |

OTHER PUBLICATIONS

Libert et al. "Signature Schemes with Efficient Protocols and Dynamic Group Signatures from Lattice Assumptions." International Conference on the Theory and Application of Cryptology and information Security. Nov. 2016. p. 373-403 (Year: 2016).*

J. Groth "Short Non-Interactive Zero Knowledge Proofs" Proceedings of Asiacrypt 2010.

B. Parno et al "Pinocchio: Nearly Practical Verigiable Computation" Proceedings of IEEE Jun. 24, 2013.

M. Veeningen "Pinocchio Based Adaptive Zk-Snarks and Secure Correct Adaptive Function Evaluation" Proceedings of Africacrypt 2017.

S. Asadova "Privacy Preserving DNA Sequence Alignment" Master Thesis Sep. 25, 2017 p. I-68.

International Search Report and Written Opinion from PCT/EP2020/070497 mailed Jan. 28, 2021.

* cited by examiner

SUMMARIZING A GENOMIC DATA ENTRY

CROSS REFERENCE TO RELATED APPLICATIONS

This application is a U.S. national phase application of International Application No. PCT/EP2020/070497 filed Jul. 21, 2020, which claims the benefit of PCT/CN2019/097490 filed July 124, 2019 and EP application Serial No. 19194491.7 filed on Aug. 29, 2019 and is incorporated herein by reference.

FIELD OF THE INVENTION

The invention relates to a device for determining a summary of a genomic data entry, and to a device for checking such a summary. The invention further relates to computer-implemented methods corresponding to the devices. The invention also relates to a computer-readable storage medium.

BACKGROUND

As microarray and DNA sequencing technologies are becoming better and better, the possibilities to easily and cheaply perform genotyping and genome sequencing are increasing. This is opening a whole range of possibilities to put DNA information to greater use, e.g., for medical research, personalized diagnosis and therapy, and personal risk prediction. In particular, it is getting easier for end users to get access to their own DNA, for example, by using one of the increasing number of companies that is offering DNA sequencing as a service, or, in the near future, by using portable DNA sequencing devices. At the same time, the amount of other companies offering to provide services or otherwise use such DNA of end users is increasing. A key question in this changing landscape is how to enable the exchange of genomic information between parties in a secure and privacy-preserving way.

In US patent application US 2015/0154646 A1, a system is proposed in which genome wide sequences, sequence related metadata, and other private data of users are stored in a database. A party wishing to obtain genomic data puts in a request comprising one or more subject criteria and a price to be paid. The subject criteria are compared with the user data from the database, and matching users receive a notification of a match. In response to the notification, the users may choose to authorize sharing parts of their data.

However, centralized set-ups for the exchange of genomic information such as the one proposed in US 2015/0154646 A1 suffer from a number of disadvantages. Because all the sensitive data is stored in a single database, this database becomes an attractive target for hackers, thus introducing a significant security risk. Moreover, especially in settings many different people or organizations want to make their genomic information available, and many other people or organizations want to obtain the information, it becomes hard to find an organization that all parties involved can trust. For these reasons, there is a desire in the industry to move more and more towards the use of private encrypted genomic data. For example, parties may encrypt their genomic data with a secret decryption key. Even when storing the genomic data elsewhere, e.g., on a centralized platform or on the cloud, parties may keep the decryption key and only share it when agreement to exchange the genomic information has been reached. Such developments can enable novel business models, but at the same time, they cause a need for improved cyber security techniques for storing, annotating and selling encrypted genomic data.

SUMMARY OF THE INVENTION

As the inventors realized, one of the problems arising when offering genomic data that is encrypted, is that the encryption of the data may make it difficult for parties interested in obtaining the genomic data to ascertain the contents and value of the genomic information. For example, in case the genomic information is being sold, encrypting the genomic data can make it hard for a potential buyer to decide whether it is worthwhile to but the genomic information and for how much. Accordingly, it would be desirable to provide technical means to allow interested parties to assess genomic information, while also offering security and confidentiality.

These and other problems are addressed by the device for determining a summary of a genomic data entry as defined by the claims. Such a genomic data entry may describe one or more genomic sequences, e.g., of a human or other organism. For example, the genomic data may represent the full sequenced genome of the organism or parts of it, e.g., at least 10%, at least 25%, or at least 50% of the genome. Various known ways of encoding the genomic data entry are possible, e.g., by means of a binary alignment map (BAM) or variant call format (VCF) file, as discussed in more detail later.

The summary being determined may be for offering the genomic data entry to one or more other parties. For example, the summary may be for offering the genomic data entry on a marketplace, e.g., in the form of an auction of the genomic data entry. The parties to which the data is offered may be referred to herein as the "interested parties". These interested parties can be from a predefined set, e.g., a set of medical practitioners or institutions associated with the marketplace. However, this is not necessary, in that it is also technically possible to auction off the data to any highest bidder. In any case, the device which determines the summary typically does not need to know the identity of the interested parties when determining the summary.

Interestingly, the summary of the genomic data entry may indicate whether the genomic data entry satisfies one or more predefined properties. As is known in the art, genomic data may be characterized particularly well by its satisfaction of such predefined properties, and the one or more interested parties may determine based at least in part on, and preferably based just on, the satisfaction of such predefined properties whether or not it is desirable to obtain the genomic data entry and/or for what reward. For example, a predefined property may indicate an amount of deviation from a reference genome, a quality of the genomic data entry, etcetera.

In some embodiments, the predefined properties are binary properties, meaning that the property is either satisfied or not satisfied for a given genomic data entry, e.g., some or all predefined properties may be binary predicates on the genomic data entry. In other embodiments, some or all predefined properties may have parameters and may thus be binary predicates on the genomic data entry given the values of the parameters, e.g., the amount of deviation from the reference genome or the value of the quality metric of the genomic data entry may be parameters.

In order to be able to provide a summary of the genomic data entry that indicates whether the genomic data entry satisfies the predefined properties, without disclosing the genomic data entry itself, the inventors devised to use two cryptographic tools: cryptographic commitments and non-interactive zero-knowledge proofs.

In particular, a device for determining a summary may obtain a cryptographic commitment to the genomic data entry. Here, the term "cryptographic commitment" is understood to refer to a representation of the genomic data entry that keeps the genomic data entry hidden, but allows to reveal the genomic data entry at a later stage. Such commitments are typically "hiding" in the sense that it is hard, e.g., computationally infeasible, for the recipient, in this case the interested parties, to derive the genomic data entry just from the commitment, but also "binding" in the sense that it is hard, e.g., computationally infeasible, for the party determining the commitment to change which value was committed to after having computed the commitment. In other words, by sharing the commitment to the genomic data entry with other parties, a party may fix the value of the genomic data entry to be revealed later, without at that point already revealing this value.

Various options for such commitments are known in the field of cryptography per se. For example, the commitment to the genomic data entry may comprise a hash of the genomic data entry, e.g., a cryptographic hash such as SHA1 or SHA2. Although such a hash can typically be efficiently computed for a given genomic data entry, on the other hand, given a hash it is typically hard to determine another input to the hash function that provides the same outcome. The genomic data entry that was committed to, may be revealed to another party by providing the genomic data entry to that other party. The other party can then check that the genomic data entry gives the same hash and, since it is normally hard to determine another input to the hash function giving the same output, the other party may thus be confident that the revealed genomic data entry was the same value that was originally committed to.

It is noted that a hash may optionally include a random value, sometimes also called a blind or a salt. The use of a random value may not be necessary to hide the genomic data since the genomic data is relatively large and therefore hard to guess in its entirety. Still, a random value may ensure that every time a genomic data entry is committed to, the resulting commitment is likely different, e.g., preventing linking between hashes used in different contexts. When revealing the genomic data entry, the random value may be revealed as well.

Apart from hashes, other types of cryptographic commitments may be used as well. For example, the cryptographic commitment may comprise an encryption of the genomic data entry, e.g., with a randomly generated decryption key. The genomic data entry may be revealed by revealing the decryption key. Other types of commitments are also possible and several are discussed elsewhere. In various contexts, it is preferable to use a constant-size commitment, e.g. a commitment whose size is independent of the size of the genomic data entry, or at least a commitment with size sublinear in the size of the genomic data entry. Since genomic data is often large and the commitments may be shared among many parties, keeping their size down is particularly useful. For example, a hash function may provide a constant-size representation; other examples are also provided throughout.

Interestingly, the device may also, for each satisfied property of the one or more predefined properties, construct a non-interactive zero-knowledge proof (NIZK). The NIZK may prove that the cryptographic commitment commits to a genomic data entry satisfying the satisfied property. NIZKs are a type of zero-knowledge proof Zero-knowledge proofs are known in the field of cryptography per se as a way to let a proving party prove to a verifying party that the proving party knows a certain value satisfying a certain property $\phi$. In this case, the device may construct a NIZK for each satisfied predefined property, proving that the cryptographic commitment commits to a genomic data entry satisfying the satisfied property, in other words, the NIZK may prove knowledge of a genomic data entry that satisfies the satisfied property and that, when computing a cryptographic commitment to the genomic data entry, gives the cryptographic commitment. Interestingly, it is known from cryptography that for various statements $\phi$, proving such statements $\phi$ is possible without having to reveal the value itself. In general, such a proof may involve a sequence of interactions, e.g., involving one or more queries by the verifying party that are answered by the proving party, that in the end convince the verifying party that the proving party indeed knows a correct value x. As an abstract example of the concept of zero-knowledge proofs, the "Ali Baba cave" example as discussed on https://en.wikipedia.org/w/index.php?title=Zero-knowledge_proof&oldid=901394099 (incorporated herein by reference) is referred to. In the present case, the zero-knowledge proof may be a non-interactive zero-knowledge proof, e.g., a proof for a particular piece of genomic data may comprise a message included in the summary that can be verified by an interested party, optionally based on verification key material.

The constructed NIZKs may then associated with the cryptographic commitment to obtain a summary of the genomic data entry. Effectively, the summary as provided herein may provide a reference to the genomic data entry being summarized, in the form of the cryptographic commitment, which is labelled with metadata providing assertions about this genomic data entry. Due to the way cryptographic commitments and non-interactive zero-knowledge proofs are used in this summary, a degree of assurance about the genomic data entry may be achieved. In particular, the genomic data entry may be offered to interested parties with a guarantee that, when the genomic data entry corresponding to the summary is provided, it satisfies the predefined properties claimed in the summary. Interested parties may obtain the summary and verify the one or more NIZKs to check that, before obtaining the data, the genomic data entry satisfies respective predefined properties proven by the NIZKs. In that sense, the summary may be seen to provide fraud-proof assertions about the genomic data entry.

Optionally, the device that determines the summary, is also configured to open the cryptographic commitment to a party that is to obtain the genomic data entry. For example, the device may select which party is to obtain the genomic entry, e.g., by selecting a party having submitted a highest bid in an auction. The device may also receive the selection of which party is to obtain the genomic entry. The opening of the commitment may be performed in various ways depending on the commitment scheme used, e.g., the opening may comprise providing the genomic data entry, and optionally a salt, as a hash preimage; providing an encryption key used to encrypt the genomic data entry, etc. The party obtaining the opening may verify it with respect to the commitment to check whether the correct data is received. Interestingly, verifying the predefined properties may no longer be needed by virtue of the party having checked the NIZKs at an earlier stage. Accordingly, by first providing a summary with a commitment and then opening the commitment, a two-stage process of providing the genomic data entry to interested parties may be provided that allows to determine in a privacy-preserving way whether to exchange data while also providing guarantees about the genomics data that may be transferred later.

In general, various architectures may be envisaged in which such a two-stage process may be beneficially applied to improve exchange of genomic data. In some embodiments, the summaries are used to enable a privacy-enhancing genomic data exchange. For example, the summary of the genomic data entry may be published on a digital announcement platform for offering the genomic data entry to the one or more other parties.

This is already beneficial in case the digital announcement platform is a centralized system, since less sensitive information needs to be processed by the digital announcement platform, e.g., unencrypted genomic information may not need to be stored by the digital announcement platform while interested parties may still be able to establish with confidence that genomic data they are interested in, satisfies particular properties.

In particularly beneficial embodiments, however, the digital announcement platform is a decentralized platform such as a blockchain. In such embodiments, it may be particularly important to restrict the information about the genomic data that is in the summary, since it is typically shared between many parties, yet at the same time it may be particularly important to provide technical guarantees about properties of the genomic data, since no trusted party may be available to vouch for such properties. The way cryptographic commitments and NIZKs are used to provide guarantees about the genomic data is thus particularly beneficial.

In particular, in some embodiments, the summary may be published on the digital announcement platform by providing the summary as an input to a smart contract for auctioning the genomic data entry to the one or more other parties. As also discussed elsewhere, the smart contract may be configured to verify the NIZKs, to select a highest bidder or bidders with sufficiently high bids, and/or to enable selected bidders to obtain the genomic data entry. Compared to centralized solutions, it is noted that no central party may be needed that is trusted by all parties, yet the use of smart contracts may still allow to achieve various security goals. For example, the party with the highest bid may be guaranteed to obtain the genomic data entry, and/or the obtained genomic data entry may be guaranteed to satisfy predefined properties as claimed by the summary. Parties that submit a non-winning bid, may be guaranteed that they do not need to pay. The party offering the genomic data entry may be guaranteed that the genomic data entry is only revealed to the highest bidder, and/or only if the bid amount is actually paid. In summary, by using the summary as a building block in a smart contract-based auction, a decentralized but still secure secret genomic data exchange may be achieved.

When using a digital announcement platform such as a blockchain, various ways to let the obtaining party actually obtain the genomic data entry corresponding to the published summary will be apparent. In particular, in some embodiments, the genomic data entry may be provided by providing a decryption key to a party that is to obtain the genomic data entry, e.g., the party providing the highest bid, etc. In case the cryptographic commitment comprises an encryption of the genomic data entry, the decryption key may be for decrypting this encryption. In other cases, apart from determining the summary, a device may further determine an encryption of the genomic data entry and a non-interactive zero-knowledge proof proving that the encryption corresponds to the cryptographic commitment, e.g., a proof that the encryption and the cryptographic commitment both comprise the same genomic data entry. In such cases, the decryption key may be for decrypting this encryption.

Interestingly, in some embodiments, an interested party may be configured to obtain such an encryption prior to indicating their interest in the genomic data entry, e.g., prior to submitting a bid to the smart contract. By obtaining the encryption and verifying that the encryption corresponds to the predefined properties claimed in the summary prior to indicating their interest, the interested party may obtain additional guarantees that it will actually get the genomic data entry, e.g., the party may not need to hope it still gets the genomic data entry after winning the auction but may instead automatically obtain the decryption key, e.g., as part of a settlement procedure of the auction. The NIZKs of the predefined properties in this case may guarantee that the party not just obtains the genomic data entry, but that it also satisfies the properties as claimed in the summary. Thereby, a more secure data exchange is obtained that is, e.g., more suitable for decentralized settings without a single trusted party.

Various variants to the above deployments are possible. As discussed, the party determining the summary may determine the cryptographic commitment itself or obtain it from elsewhere, e.g., from a sequencing device, or from an external sequencing service. In such cases, it may be beneficial for the device or service to digitally sign at least the genomic data entry. Such a digital signature may be included in the summary such that authenticity of the genomic data entry with respect to the device or service may be established. Interestingly, the device or service in such case does not need to vouch for the predetermined properties yet a recipient who verifies the digital signature is still sure that the predetermined properties are satisfied by the data authenticated by the device or service due to the way the cryptographic commitment, digital signature, and NIZKs are combined.

In some embodiments, a summary of a genomic data entry may be updated, e.g., by adding additional NIZKs constructed for additional properties. For example, upon an interested party indicating their interest in genomic data entries with particular properties, one or more additional NIZKs for the properties may be constructed and included in the summary. This way, the summary may be adapted dynamically to the needs of the interested parties. If the cryptographic commitment is digitally signed, such a dynamic adjustment may even be performed after the digital signing without affecting the guarantees about the properties being satisfied that are obtained by the interested parties.

Optionally, the genomic data entry may comprise one or more variations indicating how the one or more genomic sequences of the genomic data entry differ from a reference genome. As is known in the art, storing variations with respect to a reference genome is in many cases much more storage-efficient than storing genomic sequences explicitly. For example, the genomic data entry may be stored according to the encoding used in Variant Call Format (VCF) files. Even though variations essentially provide a compressed way of storing the genomics data, various relevant predefined properties of the genomic data entry can be still verified by examining the variations.

Optionally, as a predefined property, a maximum deviation from a predefined genome may be verified. The predefined genome may represent a particular patient population, e.g., patients with a particular condition or patients of interest for a particular clinical study. By verifying such a correspondence, an interested party may be able to gauge whether the summarized genomic data is suitable use in a particular study, for example. Deviation may be measured in various ways, e.g., based on the differences report provided by the LASTZ algorithm or using standard distance measures. The genomic data entry and the predefined genome may both be represented in terms of variations to the same reference genome, allowing efficient verification of correspondence of the genomic data entry with the predefined genome in terms of respective variations to the reference genome.

Optionally, the genomic data entry further comprises one or more quality values for genomic sequences described by the genomic data entry. As a predefined property, an overall quality value computed from the one or more quality values may be verified. For example, it may be verified whether the overall quality value is equal to a given quality value, e.g., given as a public parameter to the NIZK, or whether the overall quality value is at most or at least a given quality value, e.g., a predefined value or one given as a public parameter to the NIZK.

Optionally, one or more of the genomic sequences of the genomic data entry may be obtained from a genomic sequencer. For example, the genomic sequencer may be included in or connected with the device that determines the summary. The genomic sequencer may also be configured to determine a digital signature of the genomic sequences, or a compressed representation of them, as discussed elsewhere. By combining the sequencing with the determining of the summary, a system may be obtained that can autonomously collect and share genomics information.

Optionally, the cryptographic commitment may be computed by constructing a hash tree. Leaf nodes of the hash tree may correspond to portions of the genomic data entry. Hash trees are known per se in cryptography for verification of parts of a relatively large amount of data. The use of a hash tree in the cryptographic commitment may allow various predefined properties to be more efficiently proven and/or verified, e.g., presence of a particular base pair at a particular location in a genome may be proven by proving that the base pair is present in a leaf node of the hash tree and that the leaf node is indeed a leaf node of the hash tree. These computations may only involve the leaf node of the hash three and its siblings at various levels of the hash tree instead of, for example, scaling in the full size of the genomic data entry as would need to be done in recomputing its full hash. Thus, more efficient constructions and/or verification of NIZKs may be achieved.

Optionally, a NIZK for a satisfied property comprises a succinct non-interactive argument of knowledge (SNARK), sometimes also called a zero-knowledge SNARK or zk-SNARK. As is known in cryptography per se, a zk-SNARK proof may be constructed using an evaluation key and verified using a corresponding verification key. The evaluation and verification key may be generated together, based on a particular function to be computed, by a key generating party and then obtained by the devices that determine and check the summary. The key generating party is preferably a party trusted by the interested parties, e.g., a trusted third party. The use of function-dependent key material may allow zk-SNARKs to be particularly efficient, in particular, resulting in particularly small proofs. For example, the size of proofs may scale sub-linearly in, or even be independent of, the complexity of the computation required to verify the predetermined property. In particular, a proof may be smaller than 5000 bytes or even smaller than 1000 bytes. Moreover, it may be particularly efficient to verify such a proof, e.g., the verification effort may scale sub-linearly in, or even be independent of, the complexity of the computation. Since the proofs comprised in the summary may generally be verified and/or exchanged by many different parties, especially when using a decentralized digital announcement platform, the use of SNARKs may be particularly beneficial. Various other known types of zero-knowledge proof, e.g., zk-STARKs, SNARGs, etc, may be applied as well with similar advantages.

An embodiment of the method may be implemented on a computer as a computer implemented method, or in dedicated hardware, or in a combination of both. Executable code for an embodiment of the method may be stored on a computer program product. Examples of computer program products include memory devices, optical storage devices, integrated circuits, servers, online software, etc. Preferably, the computer program product comprises non-transitory program code stored on a computer readable medium for performing an embodiment of the method when said program product is executed on a computer.

In an embodiment, the computer program comprises computer program code adapted to perform all the steps of an embodiment of the method when the computer program is run on a computer. Preferably, the computer program is embodied on a computer readable medium.

Another aspect of the invention provides a method of making the computer program available for downloading. This aspect is used when the computer program is uploaded into, e.g., Apple's App Store, Google's Play Store, or Microsoft's Windows Store, and when the computer program is available for downloading from such a store.

BRIEF DESCRIPTION OF THE DRAWINGS

Further details, aspects, and embodiments of the invention will be described, by way of example only, with reference to the drawings. Elements in the figures are illustrated for simplicity and clarity and have not necessarily been drawn to scale. In the Figures, elements which correspond to elements already described may have the same reference numerals. In the drawings.

Figure 1:
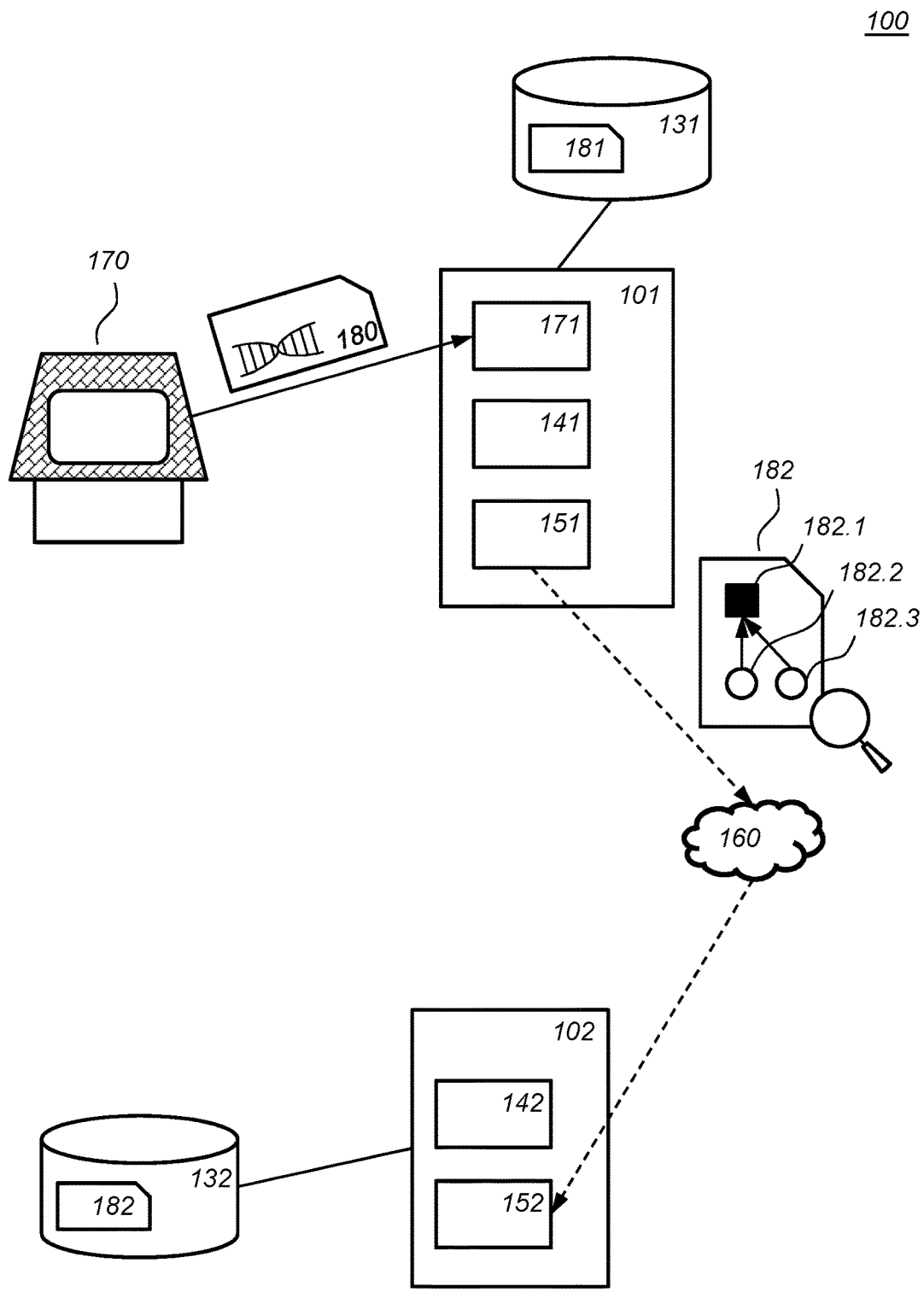
FIG. 1 schematically shows an example of an embodiment of a genomic data exchange system involving one or more predefined properties.

LIST OF REFERENCE NUMERALS 100 a genomic data exchange system
101 a summarizing device
102 a checking device
131, 132 a memory
141, 142 a processor
151, 152 a network interface
160 a computer network
170 a genomic sequencer
171 a genomic data interface
180 one or more genomic sequences
181 a genomic data entry
182 a summary
182.1 a cryptographic commitment
182.2, 182.3 a non-interactive zero-knowledge proof
201 a summarizing device
241 an encoding unit
242 a verification unit
283 a predefined set of variations
284 variations comprised in the genomic data entry
285 an encoding table
286 encoded predefined variations
287 encoded variations
288 verification output
301 a summarizing device
342 a verification unit
381 a genomic data entry
382.1 a cryptographic commitment
388 verification output
389 a variation
389' an encoded variation
401, 401' a summarizing device
402, 402', 402" a checking device
403 a key generation device
443 a circuit generation unit
444 a key generation unit
445 a circuit evaluation unit
446 a proving unit
447 a verification unit
461 a digital announcement platform
481 a genomic data entry
482 a summary
482.1 a cryptographic commitment
482.2 a succinct non-interactive argument of knowledge (SNARK)
490 a predefined property function
491 a cryptographic commitment function
492 a circuit
493 an evaluation key
494 a verification key
495 a circuit assignment
496', 496" a bid
497 data access
700 a computer readable medium
710 a writable part
720 a computer program
810 integrated circuit(s)
820 a processing unit
822 a memory
824 a dedicated integrated circuit
826 a communication element
830 an interconnect
840 a processor system

DETAILED DESCRIPTION OF THE EMBODIMENTS

While this invention is susceptible of embodiment in many different forms, there are shown in the drawings and will herein be described in detail one or more specific embodiments, with the understanding that the present disclosure is to be considered as exemplary of the principles of the invention and not intended to limit the invention to the specific embodiments shown and described.

In the following, for the sake of understanding, elements of embodiments are described in operation. However, it will be apparent that the respective elements are arranged to perform the functions being described as performed by them.

Further, the invention is not limited to the embodiments, and the invention lies in each and every novel feature or combination of features described herein or recited in mutually different dependent claims.

FIG. 1 schematically shows an example of an embodiment of a genomic data exchange system 100 involving one or more predefined properties. System 100 may comprise a device 101 for determining a summary of a genomic data entry, and a device 102 for checking the summary.

Device 101 may be for determining a summary 182 of a genomic data entry 181. Genomic data entry 181 may describe one or more genomic sequences of an organism, e.g., a human genome. Summary 182 may be for offering genomic data entry 181 to one or more other parties. In the figure, by way of explanation, one other party 102 is shown.

Device 101 may comprise a memory 131 and a processor 141. Memory 131 may be used for data and/or instruction storage. For example, memory 131 may comprise software and/or data on which processor 141 is configured to act. Memory 131 may also store genomic data entry 181. Although illustrated here as an external memory, memory 131 or part of it may also be an internal memory of device 101. Processor 141 may be implemented as one or more processor circuits, e.g. microprocessors, ASICs, FPGA and the like. Memory 131 may comprise computer program instructions which are executable by processor 141. Processor 141, possibly together with memory 131, is configured according to an embodiment of a device for determining a summary. Device 101 may also comprise a communication interface 151 arranged to communicate with other devices, in particular, device 102 for checking a summary. For example, the communication interface may comprise a connector, e.g., a wired connector, e.g., an Ethernet connector, or a wireless connector, e.g., an antenna, e.g., a Wi-Fi, 4G or 5G antenna. The communication interface may also be a storage interface to an internal or external data storage, a keyboard, an application interface (API), etc.

Device 101 may be configured to obtain genomic data entry 181. For example, device 101 may optionally comprise a genomic data interface 171 configured to obtain one or more genomic sequences 180 sequenced by an optional genomic sequencer 170. Various types of genomic sequencers may be used that may provide genomic sequences 180 in various formats that are known per se, e.g., Variant Call Format (VCF) or Binary Alignment Map (BAM). Illustrated in the figure is an ABI/Hitachi 3500 Genetic Analyzer, but various other known sequencers 170 may be used, as well, e.g., a SOLiD or Illumina DNA sequencing platform.

Sequencer 170 may also be part of device 101. Genome sequence 180 may represent a full or partial genome of a person or other organism.

Device 101 may be configured to analyse the genomic data entry 181 to verify whether it satisfies one or more predefined properties. Device 101 may also obtain a cryptographic commitment 182.1 to the genomic data entry, for example, by computing it from genomic data entry 181, getting it from sequencer 170, etcetera. For each satisfied property of the one or more predefined properties, device 101 may construct a non-interactive zero-knowledge proof (NIZK) proving that the cryptographic commitment commits to a genomic data entry satisfying the satisfied property. In this particular example, two NIZKs 182.2, 182.3 are illustrated. In general, the number of NIZKs can be at least two, at least five, at least ten, etc. Device 101 may associate the NIZKs 182.2, 182.3 with the cryptographic commitment 182.1 to obtain a summary 182 of the genomic data entry 181.

Device 102 may be for checking summary 182 of the genomic data entry in order to decide whether to obtain the genomic data entry corresponding to the summary. Device 102 may comprise a processor 142 and a memory 132. Memory 132 may be used for data and/or instruction storage. For example, memory 132 may comprise software and/or data on which processor 142 is configured to act. Although illustrated here as an external memory, memory 132 or part of it may also be an internal memory of device 102. Memory 132 may also store summary 182. Processor 142 may be implemented as one or more processor circuits, e.g. microprocessors, ASICs, FPGA and the like. Memory 132 may comprise computer program instructions which are executable by processor 142. Processor 142, possibly together with memory 132, is configured according to an embodiment of a device for checking a summary. Device 102 may also comprise a communication interface 152 arranged to communicate with other devices, in particular, device 101. For example, the communication interface may comprise a connector, e.g., a wired connector, e.g., an Ethernet connector, or a wireless connector, e.g., an antenna, e.g., a Wi-Fi, 4G or 5G antenna. The communication interface may also be a storage interface to an internal or external data storage, a keyboard, an application interface (API), etc.

Device 102 may be configured to obtain summary 182 and verify its respective one or more NIZKs 182.2, 182.3 to check that the genomic data entry committed to by commitment 182.1 satisfies respective predefined properties proven by the NIZKs 182.2, 182.3.

The devices of FIG. 1 may communicate with each other over a computer network 160. The computer network may be an internet, an intranet, a LAN, a WLAN, etc. Computer network 160 may be the Internet. The computer network may be wholly or partly wired, and/or wholly or partly wireless. For example, the computer network may comprise Ethernet connections. For example, the computer network may comprise wireless connections, such as Wi-Fi, ZigBee, and the like. Computer network 160 may comprise additional elements, e.g., a router, a hub.

The devices of FIG. 1 may have respective user interfaces, which may include well-known elements such as one or more buttons, a keyboard, display, touch screen, etc. For example, the user interface of device 102 may be arranged for accommodating user interaction for showing a summary of a genomic data entry whose NIZKs are successfully verified and obtaining a command to obtain the corresponding genomic data entry.

Figure 2:
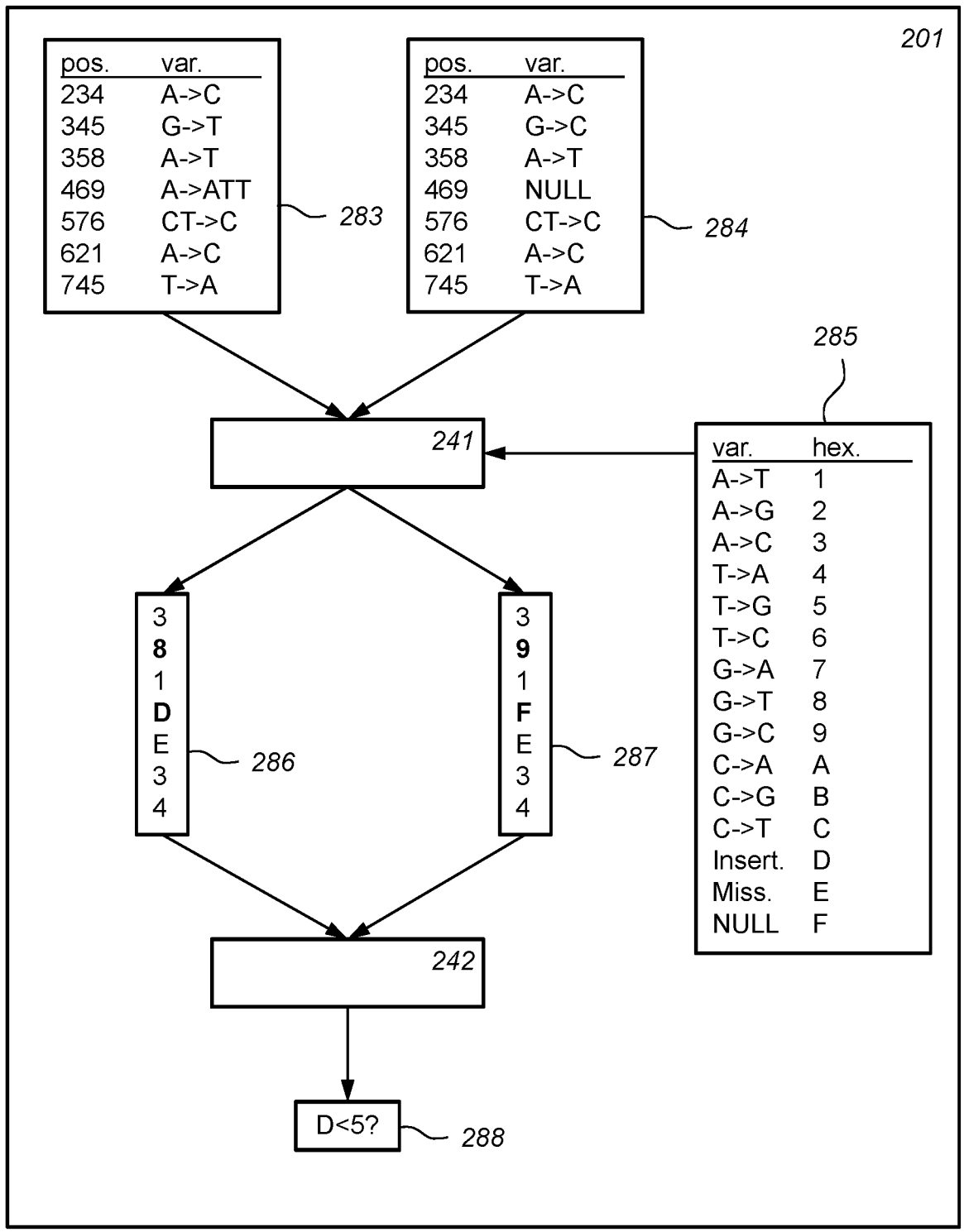
FIG. 2 schematically shows an example of an embodiment of a device for verifying, as a predefined property, a correspondence between sets of variations of genomic data.

FIG. 2 schematically shows an example of an embodiment of a device 201 for determining a summary of a genomic data entry, for example, for use in system 100 of FIG. 1. For example, device 201 may be based on device 101. FIG. 2 schematically shows functional units that may be functional units of a processor of device 201 (not shown separately). For example, FIG. 2 may be used as a blueprint of a possible functional organization of the processor. For example, the functional units shown in FIG. 2, e.g., units 241-242, may be wholly or partially be implemented in computer instructions that are stored at device 201, e.g., in an electronic memory of device 201, and are executable by a microprocessor of device 201. In hybrid embodiments, functional units are implemented partially in hardware, e.g., as coprocessors, and partially in software stored and executed on device 201. For the purpose of explication, FIG. 2 also shows various elements that may be stored by the device 201 at various stages of its operation.

As illustrated in FIG. 2, the genomic data entry to be summarized may comprise one or more variations 284 indicating how the one or more genomic sequences of the genomic data entry differ from a reference genome. As highlighted in the example, such a variation may indicate how the described genome differs from the reference genome at one or more positions. A variation may indicate, for example, one or more bases being inserted or replaced at a given position; or one or more bases being missing at the given position. Variation data may also indicate that there is no deviation to the reference genome at that given position, e.g., a NULL-type variation. Variations may be provided for a predefined set of positions, or a variant may indicate the position to which it applies, as in the figure. Variations 284 may be encoded as, or derived from, respective lines of a Variant Call Format (VCF) file.

As an illustration, shown is a variation at a position 234 where a base "A" is replaced by a base "C"; a variation at a position 345 where a base "G" is replaced by a base "C"; a variation at a position 358 where a base "A" is replaced by a base "T"; a variation at a position 469 indicating that no deviation to the reference genome is present at that position in the genomic data entry; a variation at a position 576 indicating a replacement of bases "CT" by base "C"; a variation at a position 621 indicating a replacement of a base "A" by a base "C"; and a variation at a position 745 indicating a replacement of a base "T" by a base "A".

Various predefined properties may be verified based on genomics entries represented as variations. In this particular example, it is shown how, as a predefined property, a correspondence between a predefined set of variations 283 to the reference genome and the variations 284 to the reference genome comprised in the genomic data entry may be verified. Similarly to variations 284, also variation 283 may be encoded as or derived form a VCF file, for example. Variations 283 may be considered as a public parameter to the predefined property in the sense that the variations do not need to remain secret, e.g., they may be part of a publicly known specification of the predefined property, e.g., in particular variations 283 may be known to devices checking the summary. As above, variations 283 may comprise locations and/or corresponding variation indications, e.g., in this example, a replacement "A→C" at position 234; a replacement "G→T" at position 345; a replacement "A→T" at position 358; a replacement "A→ATT" at position 469; a replacement "CT→C" at position 576; a replacement "A→C" at location 621; and a replacement "T→A" at position 745. It is noted that the positions for which variations are recorded in sets 283 and 284 are the same in this particular example, but this is not necessary; for example, if no data is recorded in set 284 for a particular variation in set 283, this may be counted as a non-correspondence at that particular position, or similar.

Although it is possible to verify correspondence between variations, and various other types of predefined properties, based on variations represented as illustrated by box 284, the inventors realized that, interestingly, for various types of predefined properties, an even more compressed representation may be used.

Accordingly, as shown in the figure, an encoding unit 241 may be employed to map variations 284 to a sequence of encoded variation 287. Given a predefined set of positions, in this case, 234, 345, etc., the encoded variations 287 may encode respective types of modifications at the respective positions. The predefined set of positions can for example be the set of positions of predefined variations 283, of multiple sets of predefined variations of respective predefined properties, or another set of predefined variations of interest.

To perform the encoding, encoding unit 241 can for example employ an encoding table 285 to determine sequence 287. For example, for a predefined set of positions, unit 241 may determine if a variation is present in variations 284 and then map it to an encoding according to the encoding table 285. If no variation is present, a fixed encoding of a "NULL" modification, in this case, encoding "F" may be used. By way of example, in table 285 respective single-base modifications are encoded by separate encodings; all insertions have the same encoding and all missing values have the same encoding. This way, complex alterations may be somewhat simplified but still, meaningful correspondence checking can be performed. Other encodings are also possible, e.g., in a more compressed but less distinguishing encoding, all single-base modifications may be mapped to the same encoding, etcetera.

Encoding unit 241 may similarly encode the predefined set of variations 283, leading to encoded predefined variations 286.

Accordingly, predefined variations 283 and variations 284 may be effectively encoded as respective sequences of characters 286, 287 indicating modifications at given locations of the reference genome and the genomic data entry, respectively. Verification unit 242 may verify correspondence between the two by computing a difference between the sequences of characters, e.g., a Hamming distance. For example, verification unit 242 may count a number of non-corresponding characters of sequences 286, 287. Verification unit 242 may also verify that the count is at most a given threshold, for example. For example, shown in the figure is a verification output 288 representing whether Hamming distance D between sequences 286, 287 is smaller than 5. In this particular example, sequences "381DE34", 286 and "391FE34", 287 have Hamming distance 2 and so in this case, verification output 288 may indicate that the predefined property is satisfied.

A maximum deviation from a predefined genome may thus be verified particularly efficiently, although such a maximum deviation could of course also be determined otherwise, e.g., not based on variations but based on respective genomic sequences of the predefined genome and of the genomic data entry.

The correspondence, e.g., in terms of Hamming distance, e.g., a maximal Hamming distance, may be implemented using various known generic zero-knowledge proof systems. Examples are provided later. For example, the following pseudocode may be used, where variables [v] between brackets denote secret values, e.g., witnesses of the zero-knowledge proof.

| Algorithm. Check correspondence between variations. |
| --- |
| Input. Encoded predefined variations $p_1, \ldots, p_n$, 286 and encoded variations $[v_1], \ldots, [v_n]$, 287 |
| [hd] ← 0 |
| for i = 1, ..., n: |
|    [cmp] ← ($p_i \neq [v_i]$)     // return 1 if not equal, 0 if equal |
|    [hd] ← [hd] + [cmp]     // add to hamming distance |
| [check] ← ([hd] < 5)     // return 1 if hd is smaller than 5, 0 otherwise |
| assert [check] == 1 |

Figure 3A:
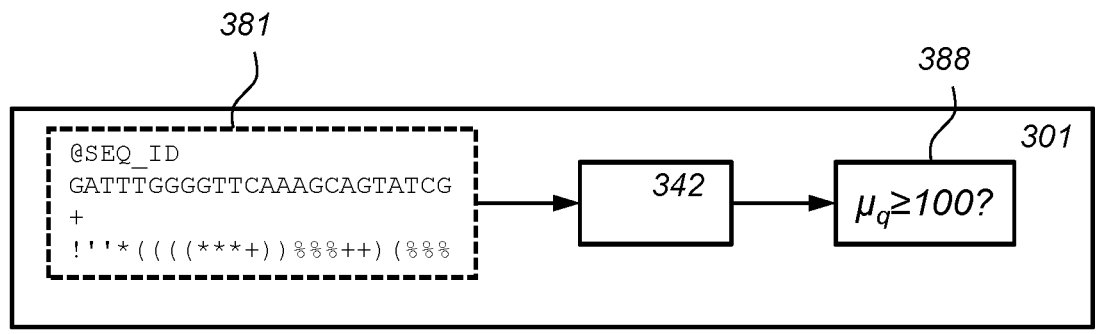
FIG. 3a schematically shows an example of an embodiment of a device for verifying, as a predefined property, an overall quality value of genomic data.

FIG. 3a schematically shows an example of an embodiment of a device 301 for determining a summary of a genomic data entry, for example, for use in system 100 of FIG. 1. For example, device 301 may be based on device 101. Similarly to FIG. 2, FIG. 3a schematically shows functional units that may be functional units of a processor of device 301 (not shown separately), and FIG. 3a also shows various elements that may be stored by the device 301 at various stages.

Shown in this figure is a genomic data entry 381 comprising one or more quality values for genomic sequences described by the genomic data entry. In this case, a portion of genomic data entry 381 is illustrated that is encoded according to the FASTQ format for storing biological sequences. Shown in the figure is a genomic sequence with sequence identifier "SEQ_ID" and contents "GAT-TTGGGGTTCAAAGCAGTATCG". The fourth line of the encoding provides quality values for respective bases of the genomic sequence. In this example, quality values running from 0x21 (33 in decimal meaning lowest quality, '!' in ASCII) to 0x72 (114 in decimal meaning highest quality; '~' in ASCII) are used. Although in this example, a respective quality value is given for each respective base pair of this part of the sequence data, it is also possible for less granular quality values to be given.

Also shown is a verification unit 342 which verifies as a predefined property an overall quality value computed from the one or more quality values. In this example, verification unit 342 may compute an average $\mu_q$ of the respective quality values of genomic data entry 381. For example, verification unit 342 may determine as a verification output 388 whether the average is at least equal to a minimum quality value, e.g., $\mu_q \geq 100$. The overall quality value may also comprise various other metrics, e.g., a minimum quality value, a maximum standard deviation over the quality values, etcetera. Various such metrics may be computed using zero-knowledge proving frameworks that are known per se, as discussed further below.

Figure 3B:
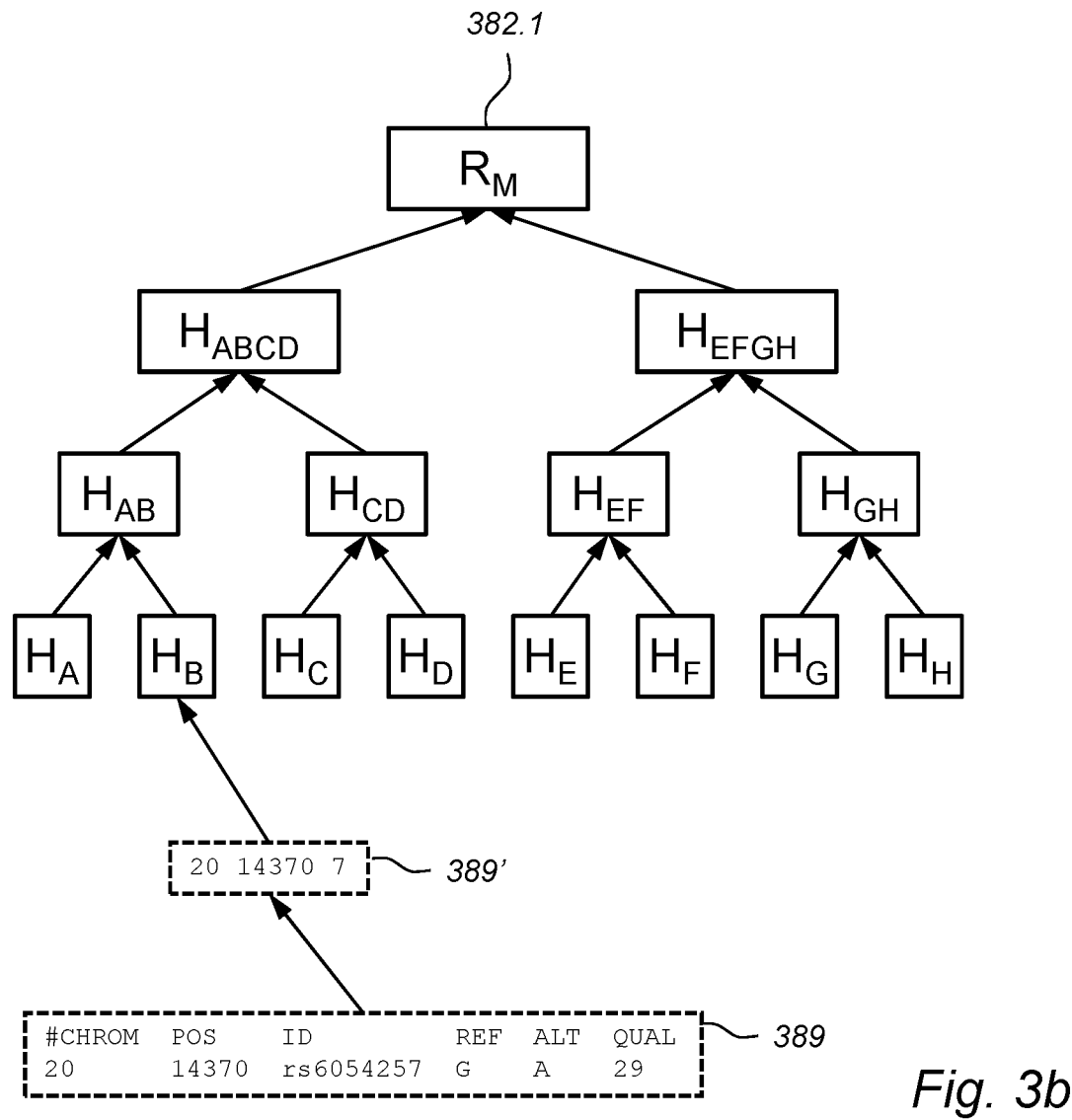
FIG. 3b schematically shows an example of verifying, as a predefined property, a predefined property based on a hash tree.

FIG. 3b illustrates various embodiments in which a cryptographic commitment to a genomic data entry is computed by constructing a hash tree, sometimes also referred to as a Merkle tree. Shown in the figure is a hash tree with eight leaf nodes $H_A$ up to $H_H$. Respective leaf nodes of the hash three may correspond to respective portions of the genomic data entry, for example, respective variations corresponding to lines of a VCF file of the genomic data entry. Internal nodes may correspond to hashes of their child nodes, e.g., node $H_{AB}$ may represent a hash of its child nodes $H_A$ and $H_B$, node $H_{EFGH}$ may represent a hash of its child nodes $H_{EF}$ and $H_{GH}$, etcetera. The hash three shown here is a complete binary tree but also non-complete and non-binary trees may be used.

Cryptographic commitment 382.1 may comprise the root of the hash tree, in this case node $R_M$, 382.1.

Considering again the leaf nodes of the hash tree, for example, a leaf node may represent a variation indicating a difference to a reference genome. For example, respective leaf nodes may correspond to respective lines of a VCF file. A line of a VCF file, e.g., line 389 shown in the figure, may be hashed directly to obtain a leaf node of the hash tree, but interestingly, also an intermediate encoding 389' may be used. For example, the intermediate encoding may represent the variation in a compressed way. Such an encoding may comprise one or more of a position of the variation, in this case, indicated by a genome number and a position in that genome, and a type of modification. For example, the type of modification may be encoded as discussed for encoding unit 241, e.g., based on encoding table 285. For example, in this figure, a substitution "G→A" of variation 389 is encoded by code "7" according to table 285.

Interestingly, the use of a hash tree may allow to prove relatively efficiently that cryptographic commitment 382.1 commits to a genomic data entry satisfying a predefined property. For example, a predefined property may be verified by verifying the property with respect to the contents of a leaf node; recomputing the top node 382.1 of the hash tree based on the siblings of the leaf node; and checking that the recomputed top node corresponds to the cryptographic commitment given in the summary. For example, a property with respect to variation 389, e.g., "a replacement variation is present at location 14370 of chromosome 20", may be verified by verifying the property with respect to encoding 389', computing hash $H_B$ from the encoding; computing hash $H_{AB}$ from hash $H_A$ and computed hash $H_B$; computing hash $H_{ABCD}$ from computed hash $H_{AB}$ and hash $H_{CD}$; computing hash $R_M$ from computed hash $H_{ABCD}$ and hash $H_{EFGH}$; and verifying that this results in the expected cryptographic commitment.

Generally, the use of hash trees for genomic data entries may be beneficial since the genomic data entries may be quite large. For example, the hash tree may have a depth of at least three or at least five. The use of a hash tree may result in a big decrease in the input size of the verification, e.g., a fixed-length input of, say, at most 1 kilobyte or even at most 256 bits may be used, rather than an input that scales in the size of the genomic data entry. Also the amount of computation needed to verify a predefined property may be greatly decreased, e.g., proving that a property is satisfied with respect to the cryptographic commitment may comprise only recomputing parts of the hash tree relevant to the predefined property, as opposed to performing a computation that scales linearly in the size of the genomic data entry.

As a detailed example, the following pseudocode may be used to verify a predefined property, in this case, a maximum Hamming distance, with respect to a hash tree:

---
Algorithm. Check maximum hamming distance using hash tree

```
snark_f(
    public: [SNPS1, Start,End,Factor, SigKey],
    private:[RM_DNA, SNPS2,PATHS2, Signature])
{
    CHECK(verifysig(RM_DNA,Signature,SigKey));
    for((SNP,PATH): (SNPS2,PATHS2) {
        CHECK(MERKLEPATH(SNP,RM_DNA,PATH));
    }
    CHECK(HAMMING(START,END,SNPS1,SNPS2) < Factor);
}
```
---

As demonstrated in the above algorithm, the public inputs to the verification may include a set of single-nucleotide polymorphisms (SNPs) to compare: a specific start and end position at which to compute the Hamming distance; an allowed difference factor; and a public key. SigKey, used to verify authenticity of the data with, e.g., a public key from a sequencing device or a trusted institution.

The secret inputs, e.g., witnesses of the zero-knowledge proof, may include a root of the hash tree, selected SNPs, paths to the roots, and a signature for the root used to verify authenticity of the data.

As shown, a Hamming distance verification algorithm may check the signature, for example, using signature verification of a known signature scheme such as ECDSA or EdDSA. The algorithm may also iterate over the SNPs and paths provided as witnesses by the prover as well as the public SNPs provided as public inputs. For each private SNP, the algorithm may check that it belongs to the signed root. In addition, the Hamming distance may be computed and compared against the given difference factor.

Figure 4A:
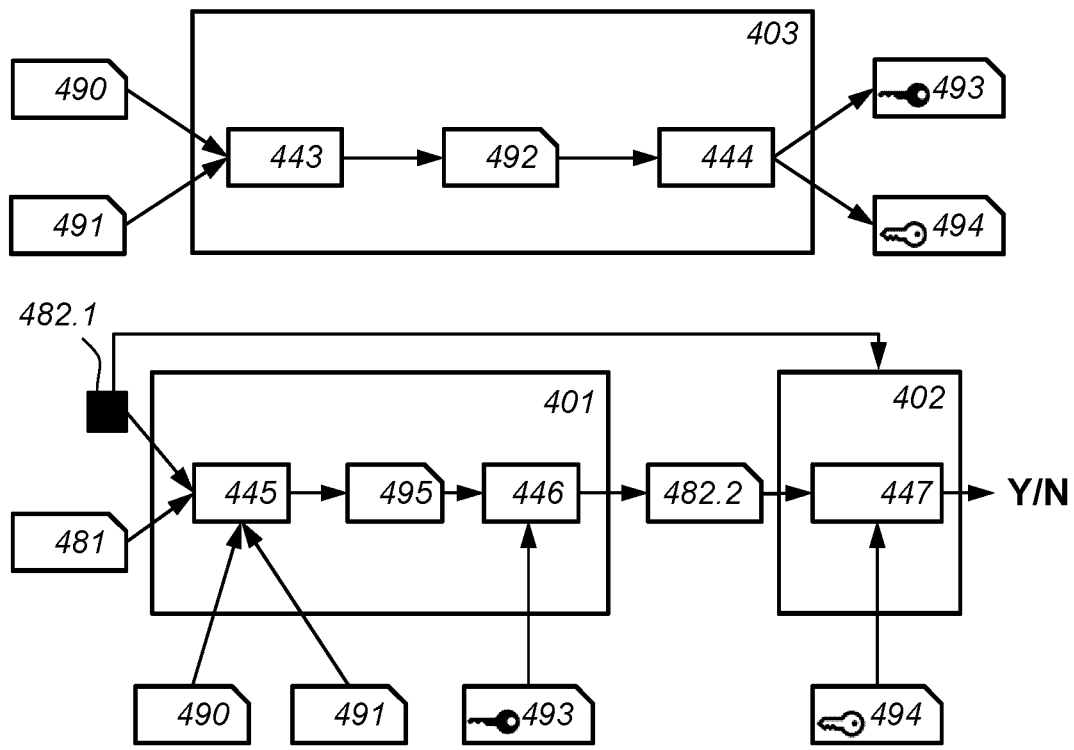
FIG. 4a schematically shows an example of an embodiment of a device for generating key material of a succinct non-interactive argument of knowledge (SNARK) for a predefined property; a device for constructing a SNARK for a predefined property; and a device for verifying the SNARK.
Figure 4B:
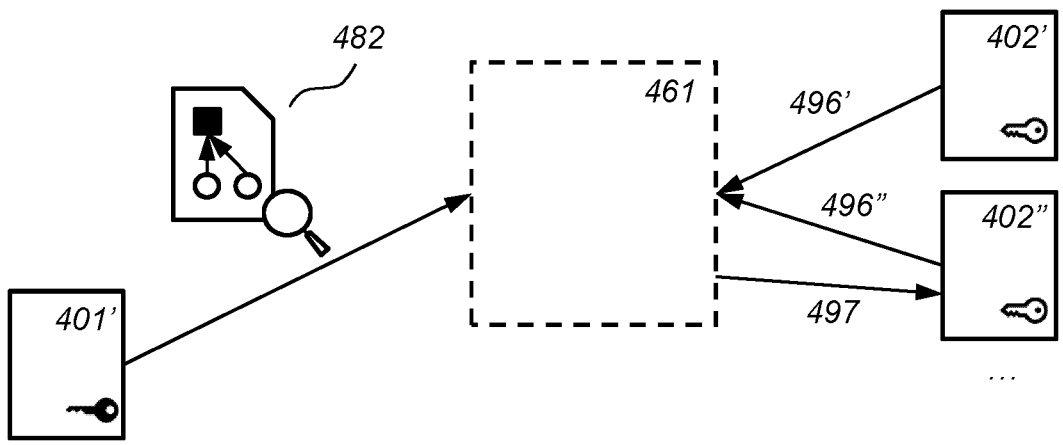
FIG. 4b schematically shows an example of an embodiment of a genomic data exchange system.

FIG. 4a schematically show examples of embodiments of respective devices that use SNARKs as proofs that genomic data entries satisfy predefined properties.

Shown is a summarizing device 401 for determining a summary of a genomic data entry 481, e.g., based on devices 101, 201, or 301 as discussed elsewhere. Also shown is a checking device 402 for checking the summary of the genomic data entry, for example, based on device 102 as discussed elsewhere.

In this example, the non-interactive zero-knowledge proof 482.2 that is constructed by device 401 and verified by device 402 is a so-called succinct non-interactive argument of knowledge (SNARK), specifically a zero-knowledge SNARK (zk-SNARK). As is known in the art of cryptography, zk-SNARKS are a type of zero-knowledge proof that can be used to establish knowledge or ownership. Generally, given a public input x, a zero-knowledge proof may be used to prove that there exists a private input y, sometimes referred to as the witness, such that a predefined predicate $\Phi(x, y)$ is satisfied. A prover typically inputs x and y and determines a proof A verifier typically inputs y and the proof to check its correctness; validity of the proof may indicate to the verifier that a value y such that $\Phi(x, y)$ is satisfied indeed exists. In the case of SNARKs, the prover typically uses an evaluation key, also known as proving key, to determine the proof. The evaluation key typically depends on the predicate $\Phi$. The verifier typically uses a verification key also depending on predicate $\Phi$.

Various zk-SNARK constructions are known from the literature, for example, as disclosed in J. Groth, "Short Non-interactive Zero-Knowledge Proofs", Proceedings of ASIACRYPT 2010 (incorporated herein by reference) or the Pinocchio system as proposed in B. Parno et al., "Pinocchio: Nearly Practical Verifiable Computation", Proceedings of IEEE S&P 2013 (incorporated herein by reference) and further elaborated upon in M. Veeningen, "Pinocchio-Based Adaptive zk-SNARKs and Secure/Correct Adaptive Function Evaluation", proceedings of AFRICACRYPT 2017 (incorporated herein by reference). The use of zk-SNARKs may be beneficial because the zero-knowledge property may preserve confidentiality while the proofs are relatively small so that, e.g., little bandwidth may be needed.

In various embodiments, zk-SNARKs are used to prove that a cryptographic commitment EHD to a genomic data entry GD satisfies a predefined property. Accordingly, a zk-SNARK may be used that can:

(i) Verify certain predefined properties ϕ of the original, e.g. unencrypted/unhashed, genome data GD. As discussed, such predefined properties may include a maximum deviation from a predefined genome, e.g., number of alleles related to a particular phenotype; an overall accuracy/quality score, etc. Accordingly, the zk-SNARK may perform the verification of such properties ϕ. As a concrete example, for example, statistical uniqueness to an agreed upon reference genome, may be implemented by designing a zk-SNARK for the LASTZ algorithm, etc.

(ii) Verify the relation between the original genome data GD and the cryptographic commitment, e.g., encrypted or hashed genomic data, EHD. For example, verifying the relation may comprise applying the chosen commitment, e.g., hash or encryption, to the original data GS inside the zk-SNARK and checking if the result matches EHD. The encryption of the genomic data GD may be performed e.g. with AES-256, hashing may be performed e.g. with SHA-256. For both algorithms, existing implementations as zk-SNARK proofs are known per se. It is noted that various zk-SNARK schemes support particularly efficient proofs with respect to particular types of commitments, e.g., commitments $C^1$ and $C^2$ of "Pinocchio-Based Adaptive zk-SNARKs and Secure/Correct Adaptive Function Evaluation" quoted above. Such commitments may be used as cryptographic commitments, e.g., instead of determining a commitment inside the proof. In case a hash tree is used for the cryptographic commitment as discussed for instance with respect to FIG. 3b, applying the commitment typically involves recomputing only a subset of the hash tree, e.g., parent nodes of one or more leaf nodes with respect to which a predefined property is verified.

As illustrated in the figure, an evaluation key 493 and a verification key 494 for the SNARK may be generated. In this example, key generation is performed by a single key generation device 403, but this not necessary, e.g., the key generation process may be performed in a distributed way using multi-party computation, etc. As input to the key generation, the device 403 may receive a definition 490 of a predefined property function and/or a description 491 of a cryptographic commitment function, e.g., corresponding to points (i) and (ii) discussed above. Key generation device 493 typically comprises a circuit generation unit 443 combining description 490 of the predefined property ϕ and description 491 of the commitment H into a circuit for an overall predicate Φ to be verified with respect to commitment c and genomic data entry d, e.g., $\Phi(c, d):=\phi(d) \wedge (H(d)=c)$. The resulting circuit 492 may be used by a key generation unit 444 to generate evaluation key 493 and verification key 494.

As a concrete example, circuit generation unit 443 may employ a logical circuit compiler such as the xjSNARK high-level zk-SNARK development framework (available at https://github.com/akosba/xjsnark/tree/47fd32e444b69c8c4a35e76c6bf8af9938340419), e.g., in combination with the libsnark library for zk-SNARKs (available at https://github.com/scipr-lab/libsnark/tree/477c9dfd07b280e42369f82f89c08416319e24ae). For example, unit 443 may compile high-level descriptions 490, 491 into a Quadratic Arithmetic Program 492. This Quadratic Arithmetic Program 492 may be input into zk-SNARK generator 444 to obtain evaluation key 493 and proving key 494. The key material may be made available to devices 401, 402 in various ways, e.g., posted on public forum, sent directly to the parties involved, etc. It is noted that the key material may be regarded as public information, e.g., security of the system may not be affected by publishing of the key material.

Once evaluation key 493 and verification key 494 are available for a particular predefined property, summarizing device 401 may construct a NIZK for the predefined property as a SNARK 482.2 based on evaluation key 493. Again, various tooling for zk-SNARKs may be used that is available per se. In particular, using the xjSNARK and libsnark tools discussed above, circuit evaluation unit 445 may determine a circuit assignment 495 corresponding to circuit 492 generated as part of key generation. Typically, this involves performing a verification of the predefined property on genomic data entry 481 and a check that the genomic data entry 481 is committed to by cryptographic commitment 482.1. Inputs, intermediate values, and/or outputs of these checks may make up circuit assignment 495. Circuit assignment 495 may then be input, together with evaluation key 493, to the proving algorithm of the zk-SNARK scheme, resulting in a proof 482.2 to be included in the summary of the genomic data entry. Checking device 402 may comprise a verification unit 447 which verifies SNARK 482.2 with respect to cryptographic commitment 482.1 using verification key 494, e.g., using the tooling provided by xjSNARK and libsnark. A successful verification of the zk-SNARK proof may indicate to checking device 402 that the predefined property is satisfied.

FIG. 4c schematically shows an examples of an embodiment of a summarizing device 401' and checking devices 402', 402". Summarizing device 401' may be based on device 101, 201, 301, or 401, for example. The checking device may be based on device 102 or 402, for example. By way of example, two checking devices are shown, although the number of checking devices can in general be arbitrary and does not need to be a priori bounded, e.g., summary 482 may be announced for anybody to access.

As shown in this figure, summarizing device 401' may publish summary 482 of the genomic data entry on a digital announcement platform 461 for offering the genomic data entry to the one or more other parties 402', 402". As discussed, one or more NIZKs of interesting genomic properties may be included as metadata to a cryptographic commitment in summary 482. Accordingly, parties who are interested in obtaining the genomic data entry that is summarized, may efficiently check the truthfulness of the metadata by verifying the NIZKs as described herein. In the proposed setup, parties offering genomic data, e.g., sellers, may thus produce proofs of interesting properties the genome data being offered, such as its statistical uniqueness, its data quality, etc. Interested parties may check these claims by verifying the proofs.

In particular, summarizing device 401' publish summary 482 on the digital announcement platform 461 by providing the summary as an input to a smart contract for auctioning the genomic data entry to the one or more other parties 402', 402". Various smart contract platforms 461 are known per se, e.g., public blockchain smart contact platforms such as Ethereum, private blockchains etc. As shown in the figure, one or more checking parties 402', 402" may determine, based on summary 482, e.g., the mentioned predefined properties, whether they are interested in obtaining the genomic data entry summarized by summary 482. Interested parties may submit a bid, e.g., shown in the figure are bid 496' of party 402' and bid 496" of party 402". For example, a bid may represent a particular monetary value offered by the party.

The smart contract may be configured to determine to which bidders to provide the genomic data, for example, to all bidders with bids above a certain threshold, to the highest bidder, to the highest bidder if its bid is above a threshold, etc. For example, the bids can be in terms of a cryptocurrency connected with the blockchain. Optionally, the smart contract is configured to verify the zero-knowledge proofs comprised in the summary as a condition for carrying out the auction. This way, the bidding process may technically guarantee to parties 402', 402", that the predefined properties are satisfied for the genomic data without the parties having to verify the zero-knowledge proofs themselves. However, in other embodiments, the verification of the proofs may also be kept outside of the smart contract, e.g., to improve efficiency of the smart contract. In such cases, the responsibility to verify the proofs in summary 482 may be assigned to the parties 402, 402" themselves.

The smart contract may also enable settling the auction, e.g., providing data access 497 to the genomic data entry to the one or more parties 402" winning the auction. In various embodiments, settling the auction may comprise provide a decryption key 497 to a winner of the auction. For example, the cryptographic commitment of summary 482 may comprise an encryption of the genomic data entry itself, or the party 402" may otherwise obtain an encryption of the genomic data entry, e.g., directly from summarizing party 401'. In the latter case, party 402" may also obtain a non-interactive zero-knowledge proof, e.g., constructed by party 401', that the encryption corresponds to the cryptographic commitment. Interestingly, party 402" may verify this proof prior to obtain assurance that it gets the data it if wins the auction. For example, this proof may be published on the digital announcement platform 461 or separately provided. In any case, party 402" obtaining the decryption key 497 may thus obtain the genomic data entry by decrypting the encryption of the genomic data entry.

Figure 5A:
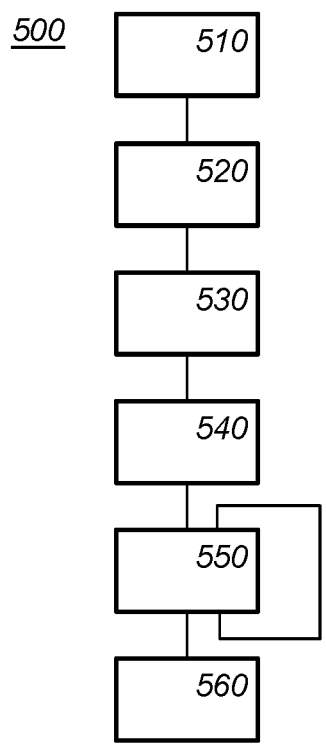
FIG. 5a schematically shows an example of an embodiment of a method of determining a summary of a genomic data entry.

FIG. 5*a* schematically shows an example of an embodiment of a computer-implemented method 500 of determining a summary of a genomic data entry describing one or more genomic sequences. The summary may be for offering the genomic data entry to one or more other parties.

Method 500 may comprise storing 510 the genomic information.

Method 500 may comprise obtaining 520 the genomic data entry.

Method 500 may comprise analysing 530 the genomic data entry to verify whether it satisfies one or more predefined properties.

Method 500 may comprise obtaining 540 a cryptographic commitment to the genomic data entry.

Method 500 may comprise, for each satisfied property of the one or more predefined properties, constructing 550 a non-interactive zero-knowledge proof (NIZK) proving that the cryptographic commitment commits to a genomic data entry satisfying the satisfied property.

Figure 5B:
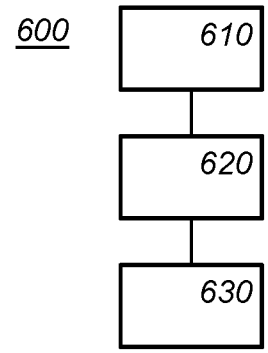
FIG. 5b schematically shows an example of an embodiment of a method of checking a summary of a genomic data entry.

Method 500 may comprise associating 560 the NIZKs with the cryptographic commitment to obtain a summary of the genomic data entry FIG. 5*b* schematically shows an example of an embodiment of a computer-implemented method 600 of checking a summary of a genomic data entry describing one or more genomic sequences for deciding whether to obtain the genomic data entry.

Method 600 may comprise storing 610 a summary of at least one genomic data entry. The summary may comprise a cryptographic commitment to the genomic data entry and one or more non-interactive zero-knowledge proofs, NIZKs. A respective NIZK may prove that the cryptographic commitment commits to a genomic data entry satisfying a respective predefined property.

Method 600 may comprise obtaining 620 the summary.

Method 600 may comprise verifying 630 the one or more NIZKs to check that the genomic data entry satisfies respective predefined properties proven by the NIZKs.

Many different ways of executing methods 500, 600 are possible, as will be apparent to a person skilled in the art. For example, the order of the steps can be varied or some steps may be executed in parallel. Moreover, in between steps other method steps may be inserted. The inserted steps may represent refinements of the method such as described herein, or may be unrelated to the method. For example, steps 540 and 550 of method 500 may be executed, at least partially, in parallel. Moreover, a given step may not have finished completely before a next step is started.

Embodiments of the methods may be executed using software, which comprises instructions for causing a processor system to perform a method 500 or 600. Software may only include those steps taken by a particular sub-entity of the system. The software may be stored in a suitable storage medium, such as a hard disk, a floppy, a memory, an optical disc, etc. The software may be sent as a signal along a wire, or wireless, or using a data network, e.g., the Internet. The software may be made available for download and/or for remote usage on a server. Embodiments of the method may be executed using a bitstream arranged to configure programmable logic, e.g., a field-programmable gate array (FPGA), to perform the method.

It will be appreciated that the invention also extends to computer programs, particularly computer programs on or in a carrier, adapted for putting the invention into practice. The program may be in the form of source code, object code, a code intermediate source, and object code such as partially compiled form, or in any other form suitable for use in the implementation of an embodiments of the method. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth.

Figure 5C:
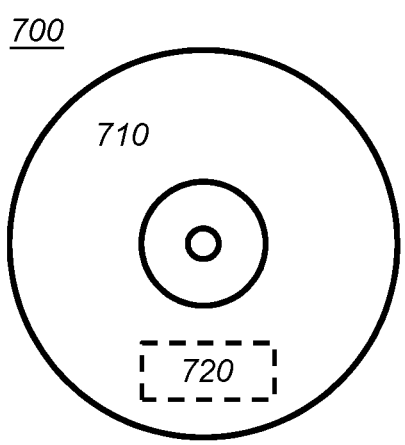
FIG. 5c schematically shows a computer readable medium having a writable part comprising a computer program according to an embodiment.

FIG. 5*c* shows a computer readable medium 700 having a writable part 710 comprising a computer program 720, the computer program 720 comprising instructions for causing a processor system to perform a method as described herein, e.g., method 500 or 600. The computer program 720 may be embodied on the computer readable medium 700 as physical marks or by means of magnetization of the computer readable medium 700. However, any other suitable embodiment is conceivable as well. Furthermore, it will be appreciated that, although the computer readable medium 700 is shown here as an optical disc, the computer readable medium 700 may be any suitable computer readable medium, such as a hard disk, solid state memory, flash memory, etc., and may be non-recordable or recordable. The computer program 720 comprises instructions for causing a processor system to perform one or said methods.

Figure 5D:
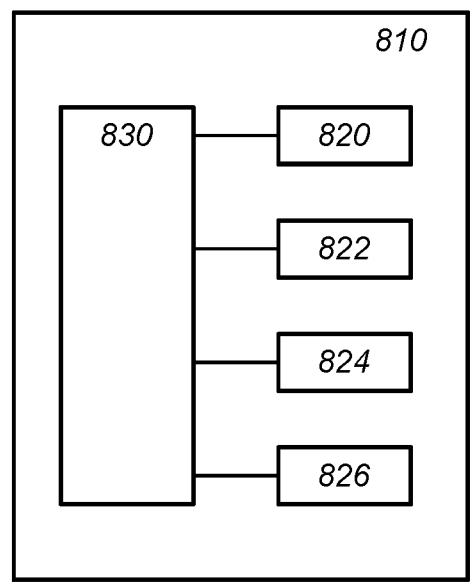
FIG. 5d schematically shows a representation of a processor system according to an embodiment.

FIG. 5*d* shows in a schematic representation of a processor system 840 according to an embodiment. The processor system comprises one or more integrated circuits 810. The architecture of the one or more integrated circuits 810 is schematically shown in FIG. 5*d*. Circuit 810 comprises a processing unit 820, e.g., a CPU, for running computer program components to execute a method according to an embodiment and/or implement its modules or units. Circuit 810 comprises a memory 822 for storing programming code, data, etc. Part of memory 822 may be read-only. Circuit 810 may comprise a communication element 826, e.g., an antenna, connectors or both, and the like. Circuit 810 may comprise a dedicated integrated circuit 824 for performing part or all of the processing defined in the method. Processor 820, memory 822, dedicated IC 824 and communication element 826 may be connected to each other via an interconnect 830, say a bus. The processor system 810 may be arranged for contact and/or contact-less communication, using an antenna and/or connectors, respectively.

For example, in an embodiment, processor system 840, e.g., a summarizing device or a checking device, may comprise a processor circuit and a memory circuit, the processor being arranged to execute software stored in the memory circuit. For example, the processor circuit may be an Intel Core i7 processor, ARM Cortex-R8, etc. In an embodiment, the processor circuit may be ARM Cortex M0. The memory circuit may be an ROM circuit, or a non-volatile memory, e.g., a flash memory. The memory circuit may be a volatile memory, e.g., an SRAM memory. In the latter case, the device may comprise a non-volatile software interface, e.g., a hard drive, a network interface, etc., arranged for providing the software.

Typically, the devices each comprise a microprocessor which executes appropriate software stored at the devices; for example, that software may have been downloaded and/or stored in a corresponding memory, e.g., a volatile memory such as RAM or a non-volatile memory such as Flash. Alternatively, the devices may, in whole or in part, be implemented in programmable logic, e.g., as field-programmable gate array (FPGA). The devices may be implemented, in whole or in part, as a so-called application-specific integrated circuit (ASIC), e.g., an integrated circuit (IC) customized for their particular use. For example, the circuits may be implemented in CMOS, e.g., using a hardware description language such as Verilog, VHDL etc.

In an embodiment, the summarizing device comprises a circuit evaluation circuit and a proving circuit. In an embodiment, the checking device comprises a verification circuit. The devices may comprise additional circuits. The circuits implement the corresponding units described herein. The circuits may be a processor circuit and storage circuit, the processor circuit executing instructions represented electronically in the storage circuits. A processor circuit may be implemented in a distributed fashion, e.g., as multiple sub-processor circuits. Part of the storage may be read-only. The circuits may also be, FPGA, ASIC or the like. A storage may be distributed over multiple distributed sub-storages. Part or all of the memory may be an electronic memory, magnetic memory, etc. For example, the storage may have volatile and a non-volatile part.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb 'comprise' and its conjugations does not exclude the presence of elements or steps other than those stated in a claim. The article 'a' or 'an' preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

In the claims references in parentheses refer to reference signs in drawings of exemplifying embodiments or to formulas of embodiments, thus increasing the intelligibility of the claim. These references shall not be construed as limiting the claim.

Features of some arrangements are set out in the following numbered paragraphs:

1. A device (101) for determining a summary (182) of a genomic data entry (181) describing one or more genomic sequences, the summary being for offering the genomic data entry to one or more other parties (102), the device comprising:
   a memory (131) configured to store the genomic data entry;
   a processor (141) configured to:
      obtain the genomic data entry (181);
      analyse the genomic data entry to verify whether it satisfies one or more predefined properties;
      obtain a cryptographic commitment (182.1) to the genomic data entry;
      for each satisfied property of the one or more predefined properties, construct a non-interactive zero-knowledge proof (NIZK; 182.2, 182.3) proving that the cryptographic commitment commits to a genomic data entry satisfying the satisfied property;
      associate the NIZKs with the cryptographic commitment to obtain a summary of the genomic data entry.

2. Device (201) according to paragraph 1, wherein the genomic data entry comprises one or more variations (284) indicating how the one or more genomic sequences differ from a reference genome.

3. Device (201) according to paragraph 2, wherein the processor is configured to verify, as a predefined property, a correspondence between a predefined set of variations (283) and the variations comprised in the genomic data entry.

4. Device (301) according to any one of the preceding paragraphs, wherein the genomic data entry (381) further comprises one or more quality values for genomic sequences described by the genomic data entry, the processor being configured to verify as a predefined property an overall quality value computed from the one or more quality values.

5. Device (101) according to any one of the preceding paragraphs, further comprising a genomic data interface (171) configured to obtain one or more genomic sequences (180) sequenced by a genomic sequencer (170).

6. Device (101) according to any one of the preceding paragraphs, wherein the processor is configured to compute the cryptographic commitment by computing a hash of the genomic data entry.

7. Device (101) according to paragraph 6, wherein the processor is configured to compute the cryptographic commitment by constructing a hash tree, leaf nodes of the hash tree corresponding to portions of the genomic data entry.

8. Device (401) according to any one of the preceding paragraphs, wherein the processor is configured to construct a NIZK (482.2) for a satisfied property by obtaining an evaluation key (493) of a succinct non-interactive argument of knowledge (SNARK) for the satisfied property and constructing the NIZK using the evaluation key.

9. Device (401') according to any one of the preceding paragraphs, wherein the processor is further configured to publish the summary (482) of the genomic data entry on a digital announcement platform (461) for offering the genomic data entry to the one or more other parties (402', 402").

10. Device (401') according to paragraph 9, wherein the processor is configured to publish the summary on the digital announcement platform by providing the summary as an input to a smart contract for auctioning the genomic data entry to the one or more other parties.

11. Device (401') according to paragraph 9 or 10, wherein the cryptographic commitment comprises an encryption of the genomic data entry or the processor is further configured to determine an encryption of the genomic data entry and a non-interactive zero-knowledge proof proving that the encryption corresponds to the cryptographic commitment, the processor being further configured to provide a decryption key to one of the other parties for decrypting the encryption.

12. A device (102) for checking a summary (182) of a genomic data entry describing one or more genomic sequences for deciding whether to obtain the genomic data entry, the device comprising:
a memory (132) configured to store a summary of at least one genomic data entry, the summary comprising a cryptographic commitment to the genomic data entry and one or more non-interactive zero-knowledge proofs, NIZKs, a respective NIZK proving that the cryptographic commitment commits to a genomic data entry satisfying a respective predefined property;
a processor (142) configured to:
obtain the summary;
verify the one or more NIZKs to check that the genomic data entry satisfies respective predefined properties proven by the NIZKs.

13. A computer-implemented method (500) of determining a summary of a genomic data entry describing one or more genomic sequences, the summary being for offering the genomic data entry to one or more other parties, the method comprising:
storing (510) the genomic information;
obtaining (520) the genomic data entry;
analysing (530) the genomic data entry to verify whether it satisfies one or more predefined properties;
obtaining (540) a cryptographic commitment to the genomic data entry;
for each satisfied property of the one or more predefined properties, constructing (550) a non-interactive zero-knowledge proof (NIZK) proving that the cryptographic commitment commits to a genomic data entry satisfying the satisfied property;
associating (560) the NIZKs with the cryptographic commitment to obtain a summary of the genomic data entry.

14. A computer-implemented method (600) of checking a summary of a genomic data entry describing one or more genomic sequences for deciding whether to obtain the genomic data entry, the method comprising:
storing (610) a summary of at least one genomic data entry, the summary comprising a cryptographic commitment to the genomic data entry and one or more non-interactive zero-knowledge proofs, NIZKs, a respective NIZK proving that the cryptographic commitment commits to a genomic data entry satisfying a respective predefined property;
obtaining (620) the summary;
verifying (630) the one or more NIZKs to check that the genomic data entry satisfies respective predefined properties proven by the NIZKs.

15. A computer readable storage medium (700) comprising transitory or non-transitory data (720) representing instructions to cause a processor system to perform the method according to paragraph 13 or 14.

The invention claimed is:

1. A device for determining a single summary of a genomic data entry describing one or more genomic sequences and one or more sequencing quality scores for the genomic sequences described by the genomic data entry, the summary being for offering the genomic data entry to one or more other parties, the device comprising:
a memory configured to store the genomic data entry;
a processor configured to:
obtain the genomic data entry;
analyse the genomic data entry to verify whether it satisfies one or more predefined properties, wherein one of the one or more predefined properties comprises an overall sequencing quality score computed from the one or more sequencing quality scores;
obtain a cryptographic commitment to the genomic data entry;
for each satisfied property of the one or more predefined properties, construct a non-interactive zero-knowledge proof (NIZK) proving that the cryptographic commitment commits to a genomic data entry satisfying the satisfied property, wherein the processor is configured to construct the NIZK for the satisfied property by obtaining an evaluation key of a succinct non-interactive argument of knowledge (SNARK) for the satisfied property and constructing the NIZK using the evaluation key, and wherein a cryptographic commitment function is utilized to construct the NIZK, the cryptographic commitment comprising an encryption of the genomic data entry;
associate the NIZKs with the cryptographic commitment to obtain the single summary of the genomic data entry.

2. Device according to claim 1, wherein the genomic data entry comprises one or more variations indicating how the one or more genomic sequences differ from a reference genome.

3. Device according to claim 2, wherein the processor is configured to verify, as a predefined property, a correspondence between a predefined set of variations and the variations comprised in the genomic data entry.

4. Device according to claim 1, further comprising a genomic data interface configured to obtain one or more genomic sequences sequenced by a genomic sequencer.

5. Device according to claim 1, wherein the processor is configured to compute the cryptographic commitment by computing a hash of the genomic data entry.

6. Device according to claim 5, wherein the processor is configured to compute the cryptographic commitment by constructing a hash tree, leaf nodes of the hash tree corresponding to portions of the genomic data entry.

7. Device according to claim 1, wherein the processor is further configured to publish the single summary of the genomic data entry on a digital announcement platform for offering the genomic data entry to the one or more other parties.

8. Device according to claim 7, wherein the processor is configured to publish the single summary on the digital announcement platform by providing the single summary as an input to a smart contract for auctioning the genomic data entry to the one or more other parties.

9. Device according to claim 7, wherein the cryptographic commitment comprises an encryption of the genomic data entry or the processor is further configured to determine an encryption of the genomic data entry and a non-interactive zero-knowledge proof proving that the encryption corresponds to the cryptographic commitment, the processor being further configured to provide a decryption key to one of the other parties for decrypting the encryption.

10. A device for checking a single summary of a genomic data entry describing one or more genomic sequences and one or more sequencing quality scores for the genomic sequences described by the genomic data entry; said device being configured to decide whether to obtain the genomic data entry, the device comprising:

a memory configured to store a single summary of at least one genomic data entry, the single summary comprising a cryptographic commitment to the genomic data entry and one or more non-interactive zero-knowledge proofs, NIZKs, a respective NIZK proving that the cryptographic commitment commits to a genomic data entry satisfying one or more respective predefined property wherein one of the one or more predefined properties comprises an overall predefined sequencing quality score, wherein the cryptographic commitment comprises an encryption of the genomic data entry;

a processor configured to:
obtain the single summary;
verify the one or more NIZKs to check that the genomic data entry satisfies respective predefined properties proven by the NIZKs;
wherein the one or more NIZKs for the satisfied property are constructed by obtaining an evaluation key of a succinct non-interactive argument of knowledge (SNARK) for the satisfied property and the one or more NIZKs are constructed using the evaluation key, and wherein a cryptographic commitment function is utilized to construct the one or more NIZKs.

11. A computer-implemented method of determining a single summary of a genomic data entry describing one or more genomic sequences and one or more sequencing quality scores for the genomic sequences described by the genomic data entry, the single summary being for offering the genomic data entry to one or more other parties, the method comprising:

obtaining the genomic data entry;
analysing the genomic data entry to verify whether it satisfies one or more predefined properties wherein one of the one or more predefined properties comprises an overall sequencing quality score;
obtaining a cryptographic commitment to the genomic data entry;
analysing the genomic data entry to verify whether it satisfies one or more predefined properties wherein one of the one or more predefined properties comprises an overall sequencing quality score;
obtaining a cryptographic commitment to the genomic data entry;
for each satisfied property of the one or more predefined properties including the overall sequencing quality score, constructing a non-interactive zero-knowledge proof (NIZK) proving that the cryptographic commitment commits to a genomic data entry satisfying the satisfied property, wherein the NIZK is constructed for the satisfied property by obtaining an evaluation key of a succinct non-interactive argument of knowledge (SNARK) for the satisfied property and constructing the NIZK using the evaluation key, and wherein a cryptographic commitment function is utilized to construct the NIZK, the cryptographic commitment comprising an encryption of the genomic data entry;
associating the NIZKs with the cryptographic commitment to obtain the single summary of the genomic data entry.

12. A non-transitory computer readable storage medium comprising transitory or non-transitory data representing instructions to cause a processor system to perform the method according to claim 11.

13. A computer-implemented method of checking a single summary of a genomic data entry describing one or more genomic sequences and one or more sequencing quality scores for the genomic sequences described by the genomic data entry, the method being configured to decide whether to obtain the genomic data entry, the method comprising:

storing a single summary of at least one genomic data entry, the single summary comprising a cryptographic commitment to the genomic data entry and one or more non-interactive zero-knowledge proofs, NIZKs, a respective NIZK proving that the cryptographic commitment commits to a genomic data entry satisfying a respective predefined property and overall predefined sequencing quality score, wherein the cryptographic commitment comprises an encryption of the genomic data entry;
obtaining the single summary;
verifying the one or more NIZKs to check that the genomic data entry satisfies respective predefined properties proven by the NIZKs;
wherein the one or more NIZKs for the satisfied property are constructed by obtaining an evaluation key of a succinct non-interactive argument of knowledge (SNARK) for the satisfied property and the one or more NIZKs are constructed using the evaluation key, and wherein a cryptographic commitment function is utilized to construct the one or more NIZKs.

* * * * *